US 6,650,729 B2

(12) United States Patent
Braess et al.

(10) Patent No.: US 6,650,729 B2
(45) Date of Patent: Nov. 18, 2003

(54) DEVICE AND METHOD FOR ADAPTING THE RADIATION DOSE OF AN X-RAY SOURCE

(75) Inventors: Henning Braess, Aachen (DE); Georg Schmitz, Wachtberg (DE); Harald Reiter, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/160,310

(22) Filed: May 31, 2002

(65) Prior Publication Data

US 2003/0035511 A1 Feb. 20, 2003

(30) Foreign Application Priority Data

May 31, 2001 (DE) ......................................... 101 32 816

(51) Int. Cl.[7] ................................................. H05G 1/44
(52) U.S. Cl. ........................................ 378/108; 378/62
(58) Field of Search .................................... 378/108, 62

(56) References Cited

U.S. PATENT DOCUMENTS

| 5,664,000 A | 9/1997 | Van Woezik et al. |
| 6,084,940 A | 7/2000 | Van Asten |
| 6,148,060 A | 11/2000 | Collins et al. |
| 6,175,614 B1 | 1/2001 | Jensen et al. |
| 2002/0114425 A1 * | 8/2002 | Lang et al. .................. 378/56 |
| 2003/0112921 A1 * | 6/2003 | Lang et al. .................. 378/54 |

FOREIGN PATENT DOCUMENTS

WO    WO 98/48600    10/1998

OTHER PUBLICATIONS

Rudolf Mester, Til Aach and Uwe Franke, "Image Segmentation Using Likelihood Ratio Test and Markov Region Shape Models"; EURASIP, 1988; pp. 837–840.

* cited by examiner

*Primary Examiner*—David V. Bruce
(74) *Attorney, Agent, or Firm*—Eugene E. Clair, Esq.

(57) ABSTRACT

The invention relates to a method and a device for adapting a radiation dose of an X-ray source (1). The X-ray source (1) irradiates an object to be examined, for example, a patient (4), so as to form an X-ray image (7) on an X-ray detector (5). The X-ray image (7) is subdivided into image regions (A–I) and each time the brightest image region is successively separated from the remaining image regions in an iterative method if its mean grey value forms an indication of the presence of direct radiation (2b) in the relevant image region. The image regions still remaining at the end of the iteration operation correspond to an image region of interest which can be taken into account by a control unit (6) so as to calculate the optimum radiation dose.

6 Claims, 2 Drawing Sheets

DEVICE AND METHOD FOR ADAPTING THE RADIATION DOSE OF AN X-RAY SOURCE

BACKGROUND

The invention relates to a method for adapting the radiation dose of an X-ray source which irradiates an object to be examined so as to form an X-ray image of the object. The invention also relates to an X-ray device for carrying out such a method.

In order to form X-ray images of an object to be examined, for example, a workpiece in the case of industrial applications or the body of a patient in the case of medical applications, the object is irradiated by means of X-rays. The transmitted X-rays are detected by an imaging detector so as to be converted into an image of the absorption density distribution. A situation is often encountered in which only a part of the fluoroscopy image is of interest for the purpose of the examination. The radiation dose of the X-ray source, therefore, should be adjusted in such a manner that such a region of interest is optimally imaged. In the case of medical applications, image regions which are not of interest occur notably when X-rays bypass the body and are incident directly on the detector (direct radiation) and hence do not contain any information concerning the absorption by the tissue. Furthermore, image regions which do not receive X-rays because of the filtering effect of absorption filters are not of interest either.

In order to adapt the X-ray dose to the X-ray image it is known to measure the overall dose arriving in the overall measuring field of the X-ray detector. When direct radiation occurs in a given, typically small part of the measuring field, a high overall dose is measured; consequently, the X-ray dose is controlled to a value which is smaller than necessary. In order to avoid this effect, it is known from WO 98/48600 to determine the histogram of the grey value distribution of the detected fluoroscopy image and to define therefrom a grey value threshold in conformity with given criteria which may be defined, for example, by fuzzy logic rules. All image points having a grey value below the defined threshold then per definition belong to the region of interest. The adaptation of the X-ray dose is subsequently performed while taking into account only the region of interest, that is, the points whose grey value is below said threshold value. This method has the drawback that exclusively the grey value of an image point decides whether or not this image point belongs to the region of interest. However, notably isolated points with deviating grey values could thus be unduly assigned to the region of interest.

SUMMARY OF THE INVENTION

Considering the foregoing it is an object of the invention to provide a method and a device for the adaptation of a radiation dose of an X-ray source which enable more correct adaptation to the regions of interest.

The method is intended to adapt the radiation dose of an X-ray source which irradiates an object to be examined, for example, the body of a patient, thus producing an X-ray image of the object. According to the method the X-ray image is subdivided into coherent image regions which have a predetermined minimum format and the radiation dose is adapted so as to be optimum for the image regions of interest. The image regions of interest are defined in that their mean grey value satisfies a given criterion.

According to the described approach the region of interest is not defined one image point or pixel after the other, but is composed of image regions of a predetermined minimum format, that is, regions comprising a minimum number of pixels. This approach ensures that the image region of interest consists of coherent parts and that no isolated islands of only one or a few pixels are included in the image region or that, conversely, no small holes of only one or a few pixels exist in the image region. The method thus produces a more realistic definition of the image region of interest, so that the subsequent adaptation of the X-ray dose on the basis of this image region of interest offers a better result. Furthermore, it is advantageous that the evaluation of image regions of a given minimum format usually can be performed faster than the evaluation of all pixels individually. The minimum format of the image regions is typically from approximately 100 to 100,000 pixels.

There are various possibilities for subdividing the X-ray image into coherent image regions of a predetermined minimum format. In the simplest case the X-ray image is subdivided into a regular grid of rectangular image regions, all of which may have the same format. Because in many cases the location in which a boundary of the image region of interest is most likely to occur is known, the format of the image regions may also be chosen so as to be smaller in such a boundary region, thus achieving a better resolution as regards the course of the boundary.

In a preferred version of the method all coherent points of the locally low-pass filtered X-ray image whose grey values lie in a given interval are combined so as to form an image region. The "coherence" of the points means that the image region forms a geometrically coherent surface, so that each pair of points of the image region can be interconnected by a line extending in the image region. The low-pass filtering of the X-ray image ensures that large brightness gradients are compensated or "spread out" so that isolated pixels of deviating brightness are avoided.

There are various possibilities for defining the given criterion which must be satisfied by the mean grey value of an image region in order to allow the image region to be an "image region of interest". In conformity with a first version this criterion consists in that the mean grey value of the corresponding image region must be larger than a minimum value and/or smaller than a maximum value. The minimum value and the maximum value may then be fixed or be defined in dependence on the relevant situation. For example, the values may be based on the mean grey value of the overall X-ray image. It is notably possible to specify only a maximum value which corresponds to a given percentage of, for example, from 100% to 200% of the mean grey value of the overall X-ray image. Image regions having a mean grey value exceeding this maximum value are then no longer considered to form part of the image region of interest. Notably image regions which receive direct radiation can thus be excluded. The exclusion of image regions whose mean grey value is below a minimum value, however, enables the exclusion of image regions from the image region of interest which correspond to zones masked by absorption filters.

According to a further version of said criterion the image regions which are (potentially) of interest are iteratively determined on the basis of the total number of image regions in that image regions which are not of interest are successively separated in conformity with the following steps:

a) separating the brightest image region from the total number of potential image regions of interest, b) determining the mean grey value of the image region separated in the step a), c) determining the mean grey value of all potential image regions of interest remaining after the separation in the step a), d) starting the iteration again with the step a) if the pair of mean grey values determined in the steps b) and c) lies outside a predetermined characteristic number of value pairs, the previously separated image region no longer being included in the number of potential image regions of interest; however, if the pair of grey values determined in the steps b) and c) lies within said characteristic number, the iteration is terminated and the number of image regions of interest is identified as the number of potential image regions of interest prior to the last execution of the step a).

The described iterative approach enables a simple determination of the image regions of interest while excluding image regions which have a very high mean grey value, for example, because of direct radiation. The dose of the X-ray source can thus be adapted also in the presence of direct radiation, without detailed knowledge of the system parameters being required for dose control.

The characteristic number used in the step d) of the above iterative method so as to make a distinction between image regions which are of interest and those which are not, can be defined in various ways, notably experimentally. Preferably this characteristic number is defined in such a manner that the pair of the mean grey values determined in the steps b) and c) lies outside this characteristic number when the ratio of the mean grey value of the separated image region to the mean grey value of the remaining, potential image regions of interest exceeds a threshold value. This threshold value may typically lie in the range of from 1.5:1 to 10:1.

The invention also relates to an X-ray device which includes the following elements:

an X-ray source for emitting X-rays, an X-ray detector for forming an X-ray image of an object irradiated by the X-ray source, a control unit for adapting the radiation dose of the X-ray source, the control unit being arranged in such a manner that it is capable of carrying out a method of the kind set forth.

An X-ray device of this kind provides a realistic definition of an image region of interest which is taken into account for the adaptation of the radiation dose of the X-ray source. The X-ray device is thus capable of producing X-ray images of higher quality of objects to be examined.

The present invention provides the foregoing and other features hereinafter described and particularly pointed out in the claims. The following description and accompanying drawings set forth certain illustrative embodiments of the invention. It is to be appreciated that different embodiments of the invention may take form in various components and arrangements of components. These described embodiments being indicative of but a few of the various ways in which the principles of the invention may be employed. The drawings are only for the purpose of illustrating a preferred embodiment and are not to be construed as limiting the invention.

BRIEF DESCRIPTION OF THE DRAWINGS

The invention will be further described with reference to examples of embodiment shown in the drawings to which, however, the invention is not restricted. In the drawings.

DETAILED DESCRIPTION

Figure 1:
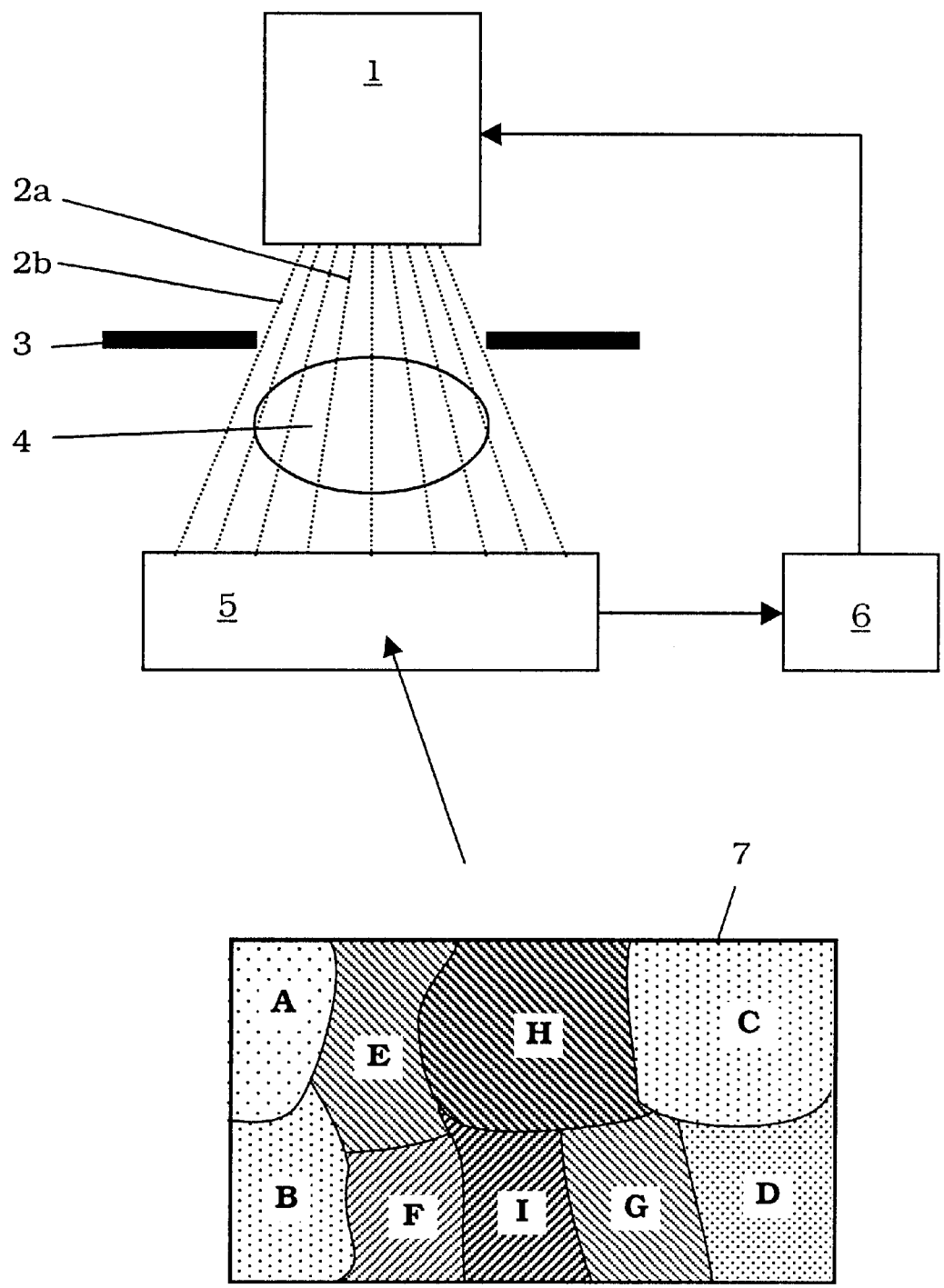
FIG. 1 is a diagrammatic representation of the components of an X-ray device in accordance with the invention and of an X-ray image subdivided into image regions.

FIG. 1 is a diagrammatic representation of the components of an X-ray device which is intended to form an X-ray image of a human body 4 in a medical application. The X-ray device consists of an X-ray source 1 which emits X-rays in the direction of the patient 4 during operation. A first part 2a of said X-rays is incident on and traverses the body 4, whereas a part 2b of the radiation bypasses the body 4 in the lateral zone. The radiation 2b is incident as so-called direct radiation on the X-ray detector 5 which is arranged underneath the patient 4; such direct radiation does not contain any information concerning the object to be examined. Absorber filters 3 can be employed to attempt and reduce the magnitude of the direct radiation 2b; however, in practice such an attempt is not perfectly successful in most cases.

The X-ray detector 5 is connected inter alia to a control unit 6 which itself is coupled to the X-ray source 1 at its output side. The control unit 6 evaluates the X-ray image produced by the X-ray detector 5 and adapts the radiation dose output by the X-ray source 1 in such a manner that it has an optimum value for the reproduction of the region of interest of the X-ray image. The method which is described in detail hereinafter is then implemented in the control unit 6 which is typically an electronic data processing unit.

According to said method, the X-ray image as produced by the X-ray detector 5 and diagrammatically shown in FIG. 1 is first subdivided into a plurality of regions A–I. In the simplest case such regions can be formed by subdividing the X-ray image 7 in checkerboard fashion into rectangular image regions of the same format. Alternatively, the image regions A–I can be defined on the basis of the grey values of the individual pixels present therein; all pixels which contact one another in an image region and whose grey value lies within an interval associated with this image region are then combined. The image regions also have a respective, given minimum format, that is, a minimum number of pixels. A further feasible method for subdividing the X-ray image is described in R. Mester, T. Aach, U. Franke: Image Segmentation Using Likelihood Ratio Tests and Markov Region Shape Models, Signal Processing IV: Theories and Applications, EUSIPCO 88, Grenoble, France (publisher: J. L. Lacoume, A. Chehikian, N. Martin, J. Malbos, pp. 104–110, September 1988).

Figure 2:
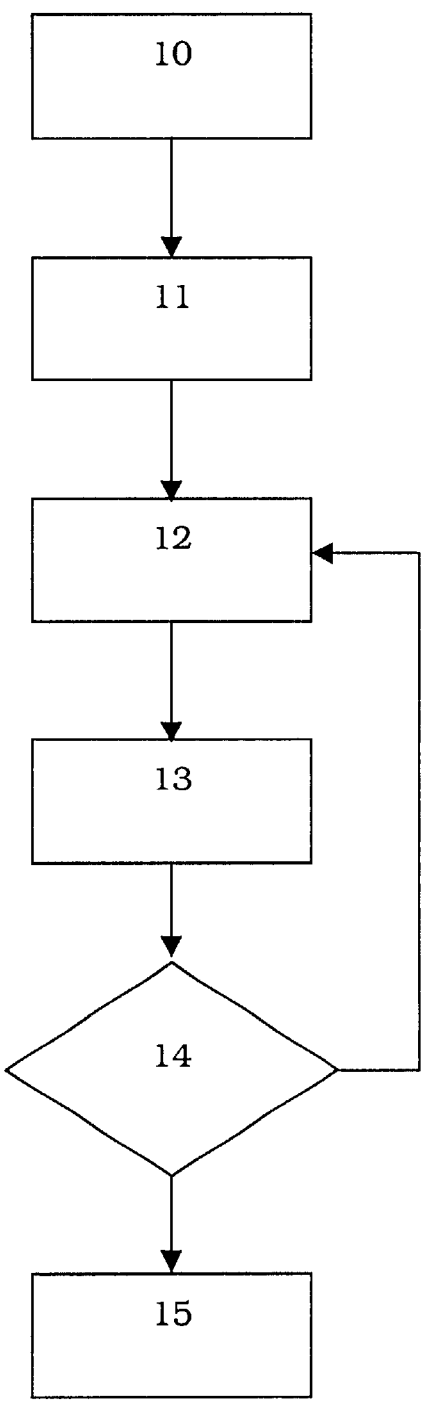
FIG. 2 shows a flowchart of the iterative method for defining the image regions of interest.

In an iterative procedure image regions whose brightness is so high that it is indicative of the presence of direct radiation in the relevant image region are successively separated. This iterative method will be described in detail hereinafter with reference to the flowchart of FIG. 2.

In the first step 10 the overall X-ray image 7 is subdivided into the image regions A–I in the described manner. In the next step 11 the image regions are sorted in conformity with their mean grey value, it being assumed that in FIG. 1 the letters A–I have been assigned to the image regions in alphabetical order in conformity with the mean grey values of these image regions (starting with the brightest grey value).

The actual iteration loop consists of the steps 12, 13 and 14. In the iteration loop a number of potential image regions of interest is successively reduced. At the beginning of the loop the number of potential image regions of interest consists of all image regions A–I of the X-ray image 7.

When the first step 12 of the iteration is carried out the first time, the image region A which exhibits the largest mean grey value of all image regions A–I is separated from the number of potential image regions of interest.

In the next step 13 the mean grey value DGW1 of the separated image region A and the mean grey value DGW2 of the remaining image regions B–I (that is, the current number of potential image regions of interest) are calculated.

In the step 14 the calculated mean grey values DGW1 and DGW2 are used to decide whether the separated image region A contains direct radiation or not. The criterion for the assumption of presence of direct radiation, for example, consists in that the ratio of the mean grey values DGW1:DGW2 is higher than a predetermined threshold value of, for example, 2:1.

If the step 14 reveals that the separated image region A contains direct radiation, it is definitively separated from the number of potential image regions of interest, and the method is continued in the step 12 for the remaining image regions B–I. During the second execution of the step 12 the next-brightest image region B is separated and so on.

However, if it is established in the step 14 that the image region separated during the last execution of the step 12 does not contain direct radiation, this image region is again added to the remaining potential image regions of interest, and in the step 15 the image region of interest is formed from said potential image regions of interest which do not contain direct radiation.

For the X-ray image 7 which is diagrammatically shown in FIG. 1, for example, the image regions A, B, C and D were separated as regions containing direct radiation during four executions of the loop 12–14, and the image region of interest was formed from the image regions E, F, G, H and I. While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

Having described a preferred embodiment, the following is claimed:

1. A method for adapting the radiation dose of an X-ray source which irradiates an object to be examined so as to form an X-ray image of the object, the method comprising the steps of:

subdividing the X-ray image into coherent image regions which have a predetermined minimum format; and adapting the radiation dose for the image regions of interest whose mean grey value satisfies a predetermined criterion.

2. The method as claimed in claim 1, wherein the step of subdividing the X-ray image into coherent image regions includes the step of combining coherent pixels having grey values within an associated predetermined interval into an associated coherent image region.

3. The method as claimed in claim 1, wherein the predetermined criterion for the image regions of interest comprises the mean grey value of an image region of interest that is at least one of higher than a minimum value and a lower than a maximum value.

4. The method as claimed in claim 1, including the step of iterative application the of the predetermined criterion for the image regions of interest to the total number of image regions, the step of iterative application comprising the steps of:

a) separating the brightest image region;

b) determining the mean grey value of the separated image region;

c) determining the mean grey value of the remaining image regions; and d) starting again with the step a) on the basis of the number of remaining image regions if the pair of mean grey values determined in the steps b) and c) lies outside a predetermined characteristic number, and otherwise identifying the remaining image regions and the last separated image region as the number of image regions of interest.

5. The method as claimed in claim 4, wherein the pair of mean grey values determined in the steps b) and c) lies outside a predetermined characteristic number when the ratio of the mean grey value of the separated image region to the mean grey value of the remaining image regions exceeds a threshold value.

6. An X-ray device comprising:

an X-ray source;

an X-ray detector for forming an X-ray image of an object irradiated by the X-ray source;

a control unit including means for subdividing the X-ray image into coherent image regions which have a predetermined minimum format; and means for adapting the radiation dose of the X-ray source for the image regions of interest whose mean grey value satisfies a predetermined criterion.

* * * * *